United States Patent [19]

Noda et al.

[11] 4,443,626
[45] Apr. 17, 1984

[54] 2,3-DIHYDRO-INDENE DERIVATIVES

[75] Inventors: Kanji Noda, Tsukushino; Akira Nakagawa; Kenji Yamagata, both of Tosu; Yoichi Nakashima, Tacharai; Masayoshi Tsuji, Tosu; Tetsuo Aoki, Kiyama; Hiroyuki Ide, Fukuoka, all of Japan

[73] Assignee: Hisamitsu Pharmaceutical Co., Inc., Tosu, Japan

[21] Appl. No.: 385,673

[22] Filed: Jun. 7, 1982

[51] Int. Cl.³ .................... C07C 79/46; C07C 59/86
[52] U.S. Cl. .................... 562/434; 562/462; 562/489; 560/51; 560/56; 424/315; 424/317
[58] Field of Search ............ 562/462, 434; 560/51, 560/56; 424/317, 315

[56] References Cited

PUBLICATIONS

Chemical Abstracts 88: 104975e, vol. 88, 1978.
Chemical Abstracts 88: 104979j, vol. 88, 1978.
Chemical Abstracts 90: 72131z, vol. 90, 1979.

Primary Examiner—Paul J. Killos
Attorney, Agent, or Firm—Bucknam and Archer

[57] ABSTRACT

Novel 2,3-dihydro-indene derivatives having remarkable anti-inflammatory effects and represented by the following formula

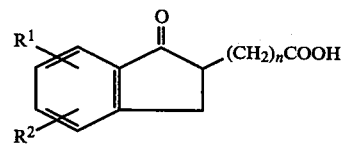

wherein $R^1$ and $R^2$ are each a hydrogen atom, halogen atom, nitro group, lower alkyl group or lower alkyloxy group with the proviso that $R^1$ and $R^2$ do not take a hydrogen atom at the same time, and n is an integer of 2–4.

20 Claims, No Drawings

2,3-DIHYDRO-INDENE DERIVATIVES

This invention relates to a novel 2,3-dihydro-indene derivative having the following general formula

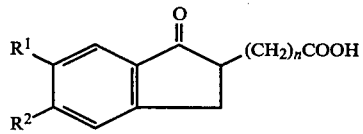

wherein n is an integer of 2–4, and $R^1$ and $R^2$ are each a hydrogen atom, nitro group, lower alkyl group or lower alcoxy group with the proviso that $R^1$ and $R^2$ are not both hydrogen.

More particularly, in the $R^1$ and $R^2$, the halogen atom is fluorine, chlorine, bromine or iodine, the lower alcoxy is methoxy, ethoxy, n-propoxy or like group and the lower alkyl group is methyl, ethyl, n-butyl, isobutyl, n-propyl or isopropyl group.

Conventional compounds which are similar to the compounds of this invention include 4-methyl-oxo-2,3-dihydro-2-indene acetic acid [Chemical Abstracts (hereinafter referred to as "C.A."), Vol. 57, 16430i], 5,6-dimethoxy-1-oxo-2,3-dihydro-2-indene acetic acid (C.A. Vol. 73, 45192n), 5-methoxy-1-oxo-2,3-dihydro-2-indene acetic acid (C.A. Vol. 67, 116739k), 4,7-dimethyl-1-oxo-2,3-dihydro-2-indene acetic acid (C.A. Vol. 74, 88156s), 5-chloro-1-oxo-2,3-dihydro-2-indene acetic acid (C.A. Vol. 88, 104975e), 5-bromo-1-oxo-2,3-dihydro-2-indene acetic acid (C.A. Vol. 90, 72131z) and 4-methoxy-1-oxo-2,3-dihydro-2-indene butyric acid (C.A. Vol. 88, 104979j). These similar compounds described in the above respective Chemical Abstracts are each disclosed as an intermediate for a certain end compound and, thus, the Chemical Abstracts neither teach nor even suggest anything about the medicinal utility of the similar compounds, not to speak of the pharmacological effects such as anti-inflammatory effect, analgesic effect, antipyretic effect, antiallergic effect, anticomplementary effect, anti-blood platelet aggregation effect and anti-hypercholesterol effect, although it is not known at all whether or not said similar compounds have such medicinal utility and pharmacological effects. It is only the process and chemical reactions for the production of the similar compounds that the Chemical Abstracts disclose.

The compounds of this invention are novel ones which have not yet described in any existing literature. They have useful pharmacological effects such as remarkable anti-inflammatory effects, that is, anaphylaxis type, cytotoxicity type, Arthus type and cell-mediated immune type antiallergic effects, and particularly they exhibit high pharmacological activity in the case of the Arthus type effect. They are useful as a drug for prevention and treatment of allergic diseases such as nephritis, rheumatism, collagenosis and autoimmune diseases. They further have anti-blood platelet aggregation effect, anti-inflammatory effect, analgesic effect, antipyretic effect, anti-hypercholesterol effect and the like, and they are therefore useful as medicines.

Conventional non-steroid type medicines having an anti-inflammatory action are typified by indomethacin. Indomethacin is frequently taken by rheumatics and the like, but it is disadvantageous in that, for example, it must be taken continuously for a long period of time and administered in a great dose thereof with the result that it raises a problem as to gastrointestinal, liver, renal and like diseases caused thereby as side effects.

In the treatment of nephritis, a hypotensive drug (such as α-methyldopa or β-blocker) is used in the existence of high blood pressure, a diuretic drug (such as Furosemide) is used in the presence of remarkable swelling and anti-cholesterol drug or the like is used in the presence of nephrosis since hypercholesteremia is caused in this case. However, any of these treatments is no more than a general symptomatic one and is not a fundamental one.

Thus the present inventors made intensive studies in an attempt to obtain novel compounds which are of non-steroid type and are effective for inflammatory diseases associated with immunity and, as a result of their studies, they synthesized 2,3-dihydro-indene derivatives having the general formula (I) previously described and found after their various studies of pharmacological effects of the novel compounds that the novel compounds inhibit an Arthus type reaction which is not inhibited by the widely-used conventional anti-inflammatory drugs. As is seen from the above, the novel compounds have remarkable pharmacological effects and are very different from the conventional non-steroid type anti-inflammatory drugs in the respect that, for example, the former have such a medicinal effect on inflammations associated with immunity.

Even in the broad conception of antiallergy, the fact that the novel compounds exhibit remarkable inhibiting effects on Arthus type inflammatory reactions indicates the utility of the novel compounds as a drug for prevention of treatment of nephritis, rheumatism, collagenosis, autoimmune diseases and the like. The novel compounds which are those of this invention, exhibit excellent medicinal effects particularly on rheumatism, that is articular rheumatism and are quite different in functional mechanism from the conventional non-steroid type anti-inflammatory drug. They further have anti-platelet aggregation, anti-inflammatory, analgesic, antipyretic, anti-hypercholesterol and like effects, exhibit a low toxicity value even in acute toxicity tests and are industrially useful as a drug which is very high in safety.

The compounds of this invention are mixed with a pharmaceutically suitable carrier or excipient to form a mixture which is then treated to obtain the mixture in the capsulate, powdery, granular, pill, tablet, suspension, emulsion, syrupy, liquid, to-be-injected, suppository, external application or like form. The thus obtained preparations may be orally or non-orally administered.

A process for the preparation of the compounds of this invention will be mentioned hereinbelow.

The compounds of this invention may be prepared in a good yield by the following process, however, this process is no more than an exemplary one and other processes similar to said exemplary one may also be used for the purpose of this invention.

Preparation A

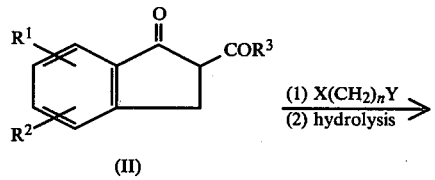

-continued
Preparation A

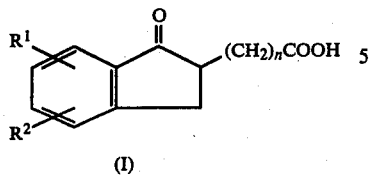

In the above formulae, $R^1$ and $R^2$ are each a hydrogen atom, halogen atom, nitro group, lower alkyl group or lower alcoxy group with the proviso that $R^1$ and $R^2$ are not both hydrogen, $R^3$ is a hydrogen atom, lower alkoxy group or lower alkoxycarbonyl group, X is a halogen atom, Y is cyano group or lower alkoxycarbonyl group and n is an integer of 2–4.

Preparation B

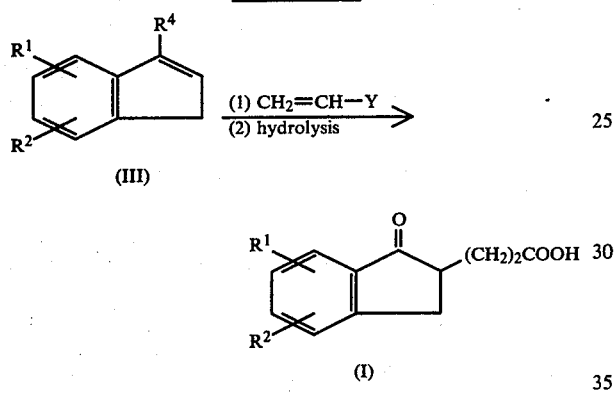

In the above formulae, $R^1$, $R^2$ and Y are as defined in Preparation A and $R^4$ is pyrrolidino, piperidino or morpholino.

Preparation C

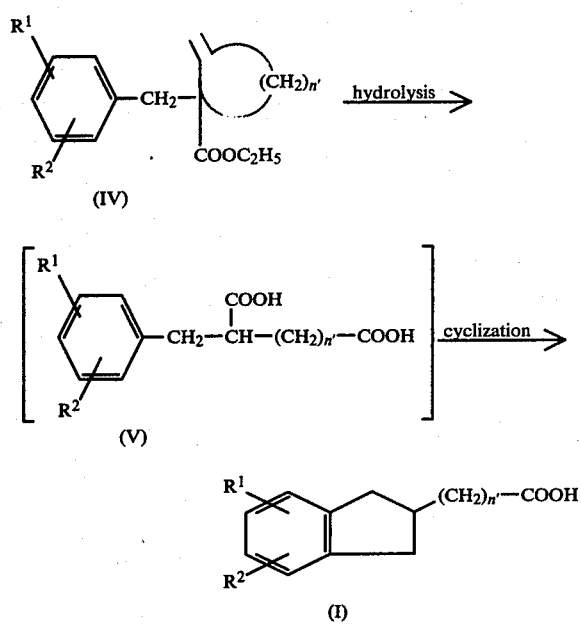

In the above formulae, $R^1$ and $R^2$ are as defined in Preparation A and n' is an integer of 3–4.

The processes as indicated in Preparations A, B and C will be explained in more detail hereinbelow.

The process as indicated in Preparation A comprises reacting a compound (II) with an alkylating agent in a solvent in the presence of an alkali or an organic amine at room temperature or, if necessary, an elevated temperature for 3–48 hours and then hydrolyzing the resulting reaction product with a mineral acid such as hydrochloric or sulfuric acid to obtain a desired compound having the general formula (I). At the time of said hydrolysis, an organic solvent such as acetic acid may be used in order to keep the reaction uniform. The alkali used herein includes sodium methylate, sodium ethylate, potassium t.-butylate, sodium amide or sodium hydride. The organic amine used herein includes triethylamine, trimethylamine or N,N-dimethylaniline. The solvent used herein includes methanol, ethanol, tetrahydrofuran, benzene, toluene, xylene, dioxane, dimethylformamide, dimethylsulfoxide or hexamethylenephosphotriamide.

The process as indicated in Preparation B comprises reacting a compound (III) with acrylonitrile or an acrylic acid lower alkyl ester in an organic solvent (such as methanol, ethanol, tetrahydrofuran, dioxane, benzene or dimethylformamide) at 30°–120° C. for 1–48 hours and, if necessary, under a nitrogen stream and then hydrolyzing the resulting reaction product with a mineral acid (such as hydrochloric or sulfuric acid) in an organic solvent such as acetic acid or with diluted hydrochloric, sulphuric acid or the like without the use of a solvent.

The process as indicated in Preparation C comprises hydrolyzing a compound having the formula (IV) with an alkali (such as sodium hydroxide, potassium hydroxide, sodium carbonate or potassium carbonate) or with a mineral acid (such as hydrochloric or sulfuric acid) to produce a compound having the formula (V). At this time, the thus produced compound (V) may be isolated if necessary or subjected to the next reaction without the isolation thereof. The compound (V) may be cyclized in one step with a condensing agent (such as polyphosphoric acid, phosphoric acid, sulfuric acid, tin tetrachloride, phosphorus oxychloride or hydrobromic acid, and acetic acid) or it may be firstly treated with a halogenating agent (such as thionyl chloride, phosphorus trichloride, phosphorus pentachloride or phosphorus tribromide) and then reacting the resulting halogenated compound with a dehalogenating agent (such as aluminum chloride, stannic chloride or zinc chloride) in an inert solvent (such as carbon disulfide or nitrobenzene) to obtain a desired compound (I).

The compounds (II), (III) and (IV) which may be used as a starting compound in this invention, may be easily obtained in accordance with the process of, for example, E. S. Stratford, Journal of Pharmaceutical Sciences, 67, 80 (1978); E. D. Bergmann, Journal of Organic Chemistry, 26, 3555 (1961); or C. K. Ingold, Journal of Chemical Society, 1954, 1204.

This invention will be better understood by the following examples.

EXAMPLE 1

2.2 g of 6-fluoro-1-oxo-2,3-dihydro-2-indene ethyl carboxylate were dissolved in 20 ml of dimethylformamide, incorporated with 0.53 g of 50% sodium hydride, agitated at room temperature for 2 hours, incorporated with 3.9 g of 3-bromo-ethyl butyrate, agitated at 90° C. for 3 hours and heated to distil off the solvent under a reduced pressure thereby obtaining a residue. The thus obtained residue was incorporated with 20 ml of acetic acid and 15 ml of a 20% solution of sulfuric acid and then refluxed for 3 hours. After the end of the reaction, the reaction mixture was incorporated with 100 ml of iced water to precipitate crystals. The crystals so precipitated were filtered off, washed with water, dried and then recrystallized from isopropyl ether to obtain 1.45 g of 6-fluoro-1-oxo-2,3-dihydro-2-indene butyric acid in the colorless needle form. The properties of the thus obtained end product are as shown below.
Melting point: 106°–107° C.
Infrared absorption spectrum $\nu c=0$: 1705 cm$^{-1}$
Molecular ion peak (Mass spectrum) M+(m/e): 236

EXAMPLE 2

2.4 g of 6-chloro-1-oxo-2,3-dihydro-2-indene ethyl carboxylate, 1.82 g of triethylamine and 20 ml of benzene were mixed together to form a mixture which was incorporated with 2.93 g of 3-bromo-ethyl butyrate and refluxed for 10 hours. The resulting reaction mixture was then freed of the solvent by distilling it off under a reduced pressure to obtain a residue which was incorporated with 20 ml of acetic acid and 15 ml of 20% sulfuric acid and reacted together under reflux for 3 hours. After the end of the reaction, the reaction mixture was incorporated with 100 ml of iced water to precipitate crystals. The crystals so precipitated were filtered off, washed with water, dried and then recrystallized from ethyl acetate to obtain 1.0 g of 6-chloro-1-oxo-2,3-dihydro-2-indene butyric acid in the colorless needle form.

The thus obtained end product had the following properties.
Melting point: 141°–142° C.
Infrared absorption spectrum: $\nu c=0$: 1706 cm$^{-1}$
Molecular ion peak (Mass spectrum) M+(m/e): 252

EXAMPLE 3

Twenty-two (22) grams of 3-pyrrolidino-5-chloroindene and 18 g of methyl acrylate were dissolved in 70 ml of dioxane, refluxed for 5 hours and freed of the solvent by distilling it off, to obtain a residue. The thus obtained residue was incorporated with 100 ml of acetic acid and 100 ml of hydrochloric acid and heated for 3 hours. After the end of the reaction, the resulting reaction mixture was freed of the solvent by distilling it off under a reduced pressure and incorporated with iced water to precipitate crystals. The crystals so precipitated were filtered off, washed with water, dried and then recrystallized from ethyl acetate to obtain 16 g of 6-chloro-1-oxo-2,3-dihydro-2-indene propionic acid in the colorless needle form.

The thus obtained end product had the following properties.
Melting point: 171°–173° C.
Infrared absorption spectrum $\nu c=0$: 1710 cm$^{-1}$
Molecular ion peak (Mass spectrum) M+(m/e): 238

EXAMPLE 4

19.2 g of 2-oxocyclohexanecarboxylic acid ethyl ester, 21.4 g of p-fluorobenzyl bromide, 7.7 g of sodium ethoxide and 200 ml of ethanol were mixed together to form a mixture which was refluxed for 2 hours, incorporated with 500 ml of water and subjected to extraction with ethyl ether. The resulting ether layer was freed of the ether to obtain a residue. The thus obtained residue was dissolved in 500 ml of 70% ethanol, incorporated with 16.1 g of potassium hydroxide, refluxed for 3 hours and hydrolyzed to obtain 26.5 g of 1-(4-fluorobenzyl)-1,5-pentane dicarboxylic acid having a melting point of 80°–81° C. in the colorless needle form. 26 g of the thus obtained compound in the needle form and 300 g of polyphosphoric acid were mixed together to form a mixture which was agitated at 100° C. for 3 hours. After the end of the reaction, the resulting reaction mixture was incorporated with iced water and subjected to extraction with ethyl acetate. The organic layer was washed with water, dehydrated and freed of the solvent by distilling it off, thereby to obtain a residue. The thus obtained residue was recrystallized from isopropyl ether to obtain 18.2 g of 6-fluoro-1-oxo-2,3-dihydro-2-indene valeric acid in the colorless platy form.

The end product so obtained had the following properties.
Melting point: 122°–123° C.
Infrared absorption spectrum $\nu c=0$: 1705, 1690 cm$^{-1}$
Molecular ion peak (Mass spectrum) M+ (m/e): 250

The end compounds indicated in the following Examples 5–20 are those which were obtained by the process as used in Examples 1–4.

EXAMPLE 5

4-fluoro-1-oxo-2,3-dihydro-2-indene propionic acid
Melting point: 103°–105° C.
Infrared absorption spectrum $\nu c=0$: 1710 cm$^{-1}$
Molecular ion peak (Mass spectrum) M+ (m/e): 222

EXAMPLE 6

6-fluoro-1-oxo-2,3-dihydro-2-indene propionic acid
Melting point: 109°–110.5° C.
Infrared absorption spectrum $\nu c=0$: 1712 cm$^{-1}$
Molecular ion peak M+ (m/e): 222

EXAMPLE 7

4-chloro-1-oxo-2,3-dihydro-2-indene propionic acid
Melting point: 107°–110° C.
Infrared absorption spectrum $\nu c=0$: 1705 cm$^{-1}$
Molecular ion peak M+ (m/e): 238

EXAMPLE 8

5-chloro-1-oxo-2,3-dihydro-2-indene propionic acid
Melting point: 184°–186° C.
Infrared absorption spectrum $\nu c=0$: 1710 cm$^{-1}$
Molecular ion peak M+ (m/e): 238

EXAMPLE 9

6-nitro-1-oxo-2,3-dihydro-2-indene propionic acid
Melting point: 125°–127° C.
Infrared absorption spectrum $\nu c=0$: 1716 cm$^{-1}$
Molecular ion peak M+ (m/e): 249

EXAMPLE 10

4,6-dichloro-1-oxo-2,3-dihydro-2-indene propionic acid
Melting point: 142°–145° C.
Infrared absorption spectrum: $\nu c=0$: 1720, 1700 cm$^{-1}$
Molecular ion peak M+ (m/e): 272

EXAMPLE 11

4-chloro-1-oxo-2,3-dihydro-2-indene butyric acid
Melting point: 102°–103° C.
Infrared absorption spectrum $\nu c=0$: 1705 cm$^{-1}$
Molecular ion peak M+ (m/e): 252

EXAMPLE 12

6-bromo-1-oxo-2,3-dihydro-2-indene butyric acid
Melting point: 155°–157° C.

Infrared absorption spectrum νc=O: 1707 cm⁻¹
Molecular ion peak M+ (m/e): 296

EXAMPLE 13

4,6-dichloro-1-oxo-2,3-dihydro-2-indene butyric acid
Melting point: 114°–116° C.
Infrared absorption spectrum νc=O: 1710, 1700 cm⁻¹
Molecular ion peak M+ (m/e): 286

EXAMPLE 14

4-chloro-1-oxo-2,3-dihydro-2-indene valeric acid
Melting point: 79°–80° C.
Infrared absorption spectrum νc=O: 1710, 1690 cm⁻¹
Molecular ion peak M+ (m/e): 266

EXAMPLE 15

5-chloro-1-oxo-2,3-dihydro-2-indene valeric acid
Melting point: 108°–110° C.
Infrared absorption spectrum νc=O: 1705, 1690 cm⁻¹
Molecular ion peak M+ (m/e): 266

EXAMPLE 16

6-chloro-1-oxo-2,3-dihydro-2-indene valeric acid
Melting point: 138°–139° C.
Infrared absorption spectrum νc=O: 1708, 1692 cm⁻¹
Molecular ion peak M+ (m/e): 266

EXAMPLE 17

6-bromo-1-oxo-2,3-dihydro-2-indene valeric acid
Melting point: 161°–163° C.
Infrared absorption spectrum νc=O: 1710, 1694 cm⁻¹
Molecular ion peak M+ (m/e): 310

EXAMPLE 18

4,6-dichloro-1-oxo-2,3-dihydro-2-indene valeric acid
Melting point: 104°–106° C.
Infrared absorption spectrum νc=O: 1710, 1695 cm⁻¹
Molecular ion peak M+ (m/e): 300

EXAMPLE 19

6-methyl-1-oxo-2,3-dihydro-2-indene butyric acid
Melting point: 123°–124° C.

The pharmacological effects of the compounds of this invention will be substantiated by the following experiments.

EXPERIMENT 1

Effect on passive Arthus reaction in rats

Groups each consisting of 5–7 male rats of Wistar strain weighing 135–155 g each were tested in this experiment in accordance with the modified method of Denk et al. [Z. Immunitaetsforsch., 138, 169 (1969)]. The rats which had been fasted for 18 hours were sensitized by injecting 0.3 ml of a 10% solution of an anti BSA rabbit serum (precipitation titer, 32 times) to them at the tail vein. Thirty minutes after their sensitization, they were each induced by hypodermically injecting 0.1 ml of an 0.025% solution of bovine serum albumin (BSA) to them at the plantar portion of their right hind paw. Three hours after having been induced, the volume of the hind paw was measured by the Fujihira et al's method [Pharmacometrics, 5, 169 (1971)] and the swelling inhibiting ratio for each test compound was calculated from the following equation. The test compounds and indomethacin (as the control) were each suspended in an 0.5% aqueous solution of tragacanth gum and the solutions obtained were orally administered at doses of 100 mg/kg (test compound) and 5 mg/kg (control) to some of the test animals, respectively, one hour before they had been induced. On the other hand, only the vehicle was administered to the remainder of the test animals.

$$\text{Swelling ratio (\%)} = \frac{\text{Foot volume 3 hours after BSA induction} - \text{Foot volume before BSA induction}}{\text{Foot volume before BSA induction}} \times 100$$

$$\text{Swelling inhibiting ratio (\%)} = \frac{\text{Swelling ratio for control group} - \text{Swelling ratio for test compound administered group}}{\text{Swelling ratio for control group}} \times 100$$

The results are as shown in Table 1.

TABLE 1

Effect on passive Arthus reaction in rats

| Test compound | Amount of administered (mg/kg) | No. of test animals | Swelling inhibiting ratio (%) |
|---|---|---|---|
| Compd of Example 1 | 100 | 6 | 26.7 |
| Compd of Example 2 | 100 | 6 | 37.7 |
| Compd of Example 3 | 100 | 5 | 13.7 |
| Compd of Example 5 | 100 | 5 | 41.7 |
| Compd of Example 6 | 100 | 7 | 39.4 |
| Compd of Example 8 | 100 | 6 | 17.5 |
| Compd of Example 11 | 100 | 5 | 13.9 |
| Compd of Example 13 | 100 | 6 | 22.5 |
| Compd of Example 14 | 100 | 5 | 18.6 |
| Compd of Example 15 | 100 | 5 | 35.3 |
| Compd of Example 16 | 100 | 6 | 16.2 |
| Indomethacin | 5 | 5 | 8.1 |

Note:
The above swelling inhibiting ratios were determined with respect to that for the control group.

EXPERIMENT 2

Test for acute toxicity on mice

Groups each consisting of 6 male mice of ddY strain weighing between 22 and 26 g were used in this experiment.

Suspensions of the test compounds and indomethacin as the control in an 0.5% aqueous solution of tragacanth were orally administered respectively to the test animals, after which the test animals had been observed for a week to find the lethality thereof. The results are as indicated in Table 2.

TABLE 2

| Test compound | Amount of administered (mg/kg) | Lethality[1] |
|---|---|---|
| Compd. of Example 1 | 2,000 | 1/6 |
| Compd. of Example 2 | 2,000 | 2/6 |
| Compd. of Example 5 | 2,000 | 2/6 |
| Compd. of Example 6 | 500 | 0/6 |
| Compd. of Example 6 | 1,000 | 0/6 |
| Compd. of Example 6 | 2,000 | 2/6 |
| Compd. of Example 13 | 2,000 | 1/6 |
| Compd. of Example 14 | 2,000 | 0/6 |
| Compd. of Example 15 | 2,000 | 0/6 |
| Indomethacin | 50 | 6/6 |

[1]Lethalities found one week after the administration.

It is apparent from the above pharmacological experimental results that the compounds of this invention are those associated with immunity, have remarkable pharmacological effects as compared with indomethacin which is typical of conventional non-steroid preparations, and exhibit low toxicity.

What is claimed is:

1. A 2,3-dihydro-indene derivative having anti-inflammatory effects and represented by the following general formula (I)

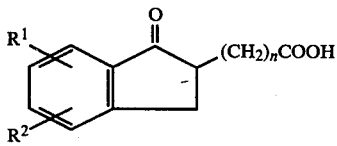

wherein $R^1$ and $R^2$ are each hydrogen, halogen, nitro, lower alkyl, with the proviso that at least one of $R^1$ and $R^2$ is other than hydrogen and n is an integer of 2–4.

2. The compound according to claim 1 which is 6-fluoro-1-oxo-2,3-dihydro-2-indene butyric acid.

3. The compound according to claim 1 which is 6-chloro-1-oxo,2,3-dihydro-2-indene butyric acid.

4. The compound according to claim 1 which is 6-chloro-1-oxo-2,3-dihydro-2-indene propionic acid.

5. The compound according to claim 1 which is 6-fluoro-1-oxo-2,3-dihydro-2-indene valeric acid.

6. The compound according to claim 1 which is 4-fluoro-1-oxo-2,3-dihydro-2-indene propionic acid.

7. The compound according to claim 1 which is 6-fluoro-1-oxo-2,3-dihydro-2-indene propionic acid.

8. The compound according to claim 1 which is 4-chloro-1-oxo-2,3-dihydro-2-indene propionic acid.

9. The compound according to claim 1 which is 5-chloro-1-oxo-2,3-dihydro-2-indene propionic acid.

10. The compound according to claim 1 which is 6-nitro-1-oxo-2,3-dihydro-2-indene propionic acid.

11. The compound according to claim 1 which is 4,6-dichloro-1-oxo-2,3-dihydro-2-indene propionic acid.

12. The compound according to claim 1 which is 4-chloro-1-oxo-2,3-dihydro-2-indene butyric acid.

13. The compound according to claim 1 which is 6-bromo-1-oxo-2,3-dihydro-2-indene butyric acid.

14. The compound according to claim 1 which is 4,6-dichloro-1-oxo-2,3-dihydro-2-indene butyric acid.

15. The compound according to claim 1 which is 4-chloro-1-oxo-2,3-dihydro-2-indene valeric acid.

16. The compound according to claim 1 which is 5-chloro-1-oxo-2,3-dihydro-2-indene valeric acid.

17. The compound according to claim 1 which is 6-chloro-1-oxo-2,3-dihydro-2-indene valeric acid.

18. The compound according to claim 1 which is 6-bromo-1-oxo-2,3-dihydro-2-indene valeric acid.

19. The compound according to claim 1 which is 4,6-dichloro-1-oxo-2,3-dihydro-2-indene valeric acid.

20. The compound according to claim 1 which is 6-methyl-1-oxo-2,3-dihydro-2-indene butyric acid.

* * * * *